United States Patent [19]

Meyer

[11] 4,148,318

[45] Apr. 10, 1979

[54] TOOL FOR SURGICAL PREPARATIONS HAVING AN INTERNAL SUPPLY OF ANTISEPTIC SOLUTION

[75] Inventor: Leonard J. Meyer, Antioch, Ill.

[73] Assignee: Abbott Laboratories, North Chicago, Ill.

[21] Appl. No.: 864,174

[22] Filed: Dec. 27, 1977

[51] Int. Cl.² .................... A61M 35/00; B43K 5/14
[52] U.S. Cl. .................................... 128/269; 401/132
[58] Field of Search .................. 128/260, 269, 268; 401/132, 134

[56] References Cited

U.S. PATENT DOCUMENTS 3,482,920  12/1969  Schwartzman ..................... 401/132
3,876,314  4/1975  Nehring ........................... 128/269 X
3,891,331  6/1975  Avery ................................. 401/132
4,027,885  6/1977  Loesser ............................ 128/269 X

FOREIGN PATENT DOCUMENTS 1161656  9/1958  France ................................. 401/134

Primary Examiner—Stephen C. Pellegrino
Attorney, Agent, or Firm—Aaron L. Hardt; Robert L. Niblack

[57] ABSTRACT

A tool for surgical preparations having an antiseptic solution contained in a reservoir thereof by a frangible cover and means affixed to a sponge integral to the tool for piercing the cover to release the solution into the sponge.

1 Claim, 11 Drawing Figures

TOOL FOR SURGICAL PREPARATIONS HAVING AN INTERNAL SUPPLY OF ANTISEPTIC SOLUTION

BACKGROUND OF THE INVENTION

The present invention relates to tools for surgical preparations and, more particularly, to such a tool with an internal supply of antiseptic solution.

Tools for surgical preparations generally include a sponge which is used by anesthesiologists to apply an antiseptic solution to a patient's skin. The sponge is dipped into an antiseptic solution in a container and swabbed onto the patient's skin to prevent live bacteria from entering an incision or wound of the skin. Several disadvantages are inherent in that procedure.

If the anethetist does not have an assistant, the solution must be poured into the container prior to the anesthetist's gloving, otherwise the anesthetist must remove the glove and replace it with a sterile glove. Occasionally, the anesthetist will forget to pour the solution, or the cart for the surgery room does not contain a bottle of the antiseptic solution and, thus the surgery is delayed while the anesthetist obtains and/or pours the solution and then regloves. On other occasions, the antiseptic solution can be spilled or splashed into the procedural tray being used for the surgery, thereby resulting in contamination of the tray and necessitating its discarding and replacement.

Accordingly, it will be apparent that a tool for surgical preparations having its own internal supply of antiseptic solution would be advantageous to anesthetists and others involved in surgical preparations.

SUMMARY OF THE INVENTION

The primary object of the present invention, therefore, is to provide an improved tool for surgical preparations, which tool will be free from the aforementioned and other disadvantages of prior devices of this type by virtue of an internal supply of antiseptic solution that can be rapidly applied by an anesthetist without the need of an assistant. Another object of the present invention is to eliminate the need for stocking an inventory of antiseptic solutions for surgical preparations.

In accordance with these and other objects, there is provided by the present invention a tool for surgical preparations having an internal supply of antiseptic solution contained in a reservoir thereof by a frangible cover and means affixed to a sponge integral to the tool for piercing the cover to release the antiseptic solution into the sponge. Preferably, the tool is made of polystyrene, the sponge is made of polyurethane and the antiseptic solution is betadine.

BRIEF DESCRIPTION OF THE DRAWING

Other objects and attendant advantages will become obvious to those skilled in the art by reading the following detailed description in connection with the accompanying drawing, wherein like reference characters designate like or corresponding parts throughout the several figures thereof and wherein.

DETAILED DESCRIPTION OF THE INVENTION

Figure 1:
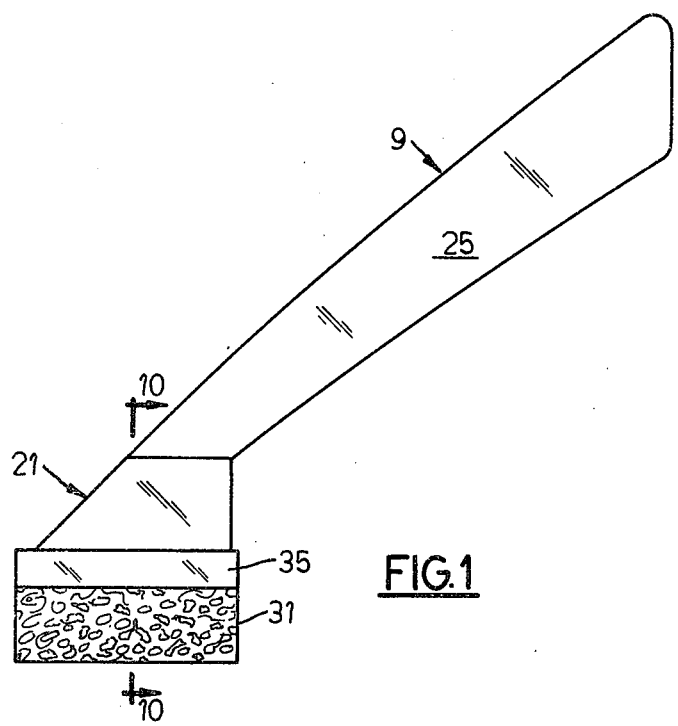
FIG. 1 is a front elevational view of a preferred embodiment of the tool for surgical preparations of the present invention.
Figure 4:
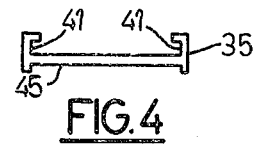
FIG. 4 is a side elevational view of the sponge holder of the device of FIG. 1.
Figure 5:
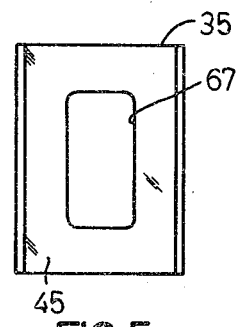
FIG. 5 is a bottom plan view of the sponge holder of FIG. 4.

Referring to the drawing, there is shown in FIG. 1 a preferred embodiment 9 of the tool for surgical preparations in accordance with the present invention. Tool 9 has a base portion 21 having a handle 25 upstanding therefrom and adapted for hand manipulation of tool 9. Base portion 21 has a bottom surface 29 adapted to receive a sponge 31 which is affixed to sponge holder 35.

Figure 2:
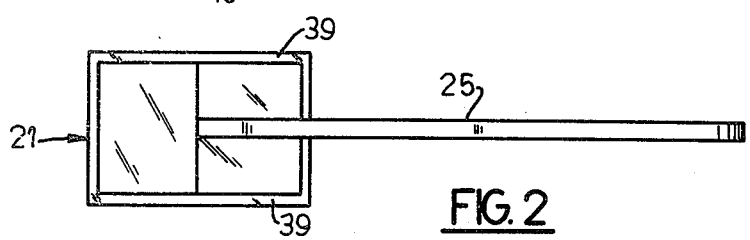
FIG. 2 is a top plan view of the base and handle of the device of FIG. 1.
Figure 3:
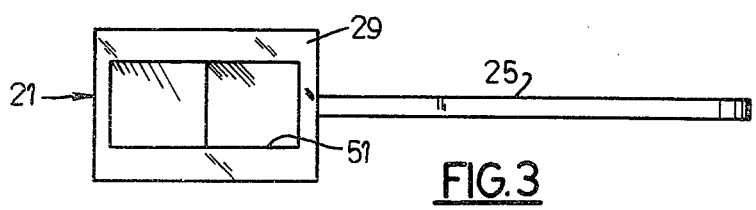
FIG. 3 is a bottom plan view of the base and handle of the device of FIG. 1.
Figures 10, 11:
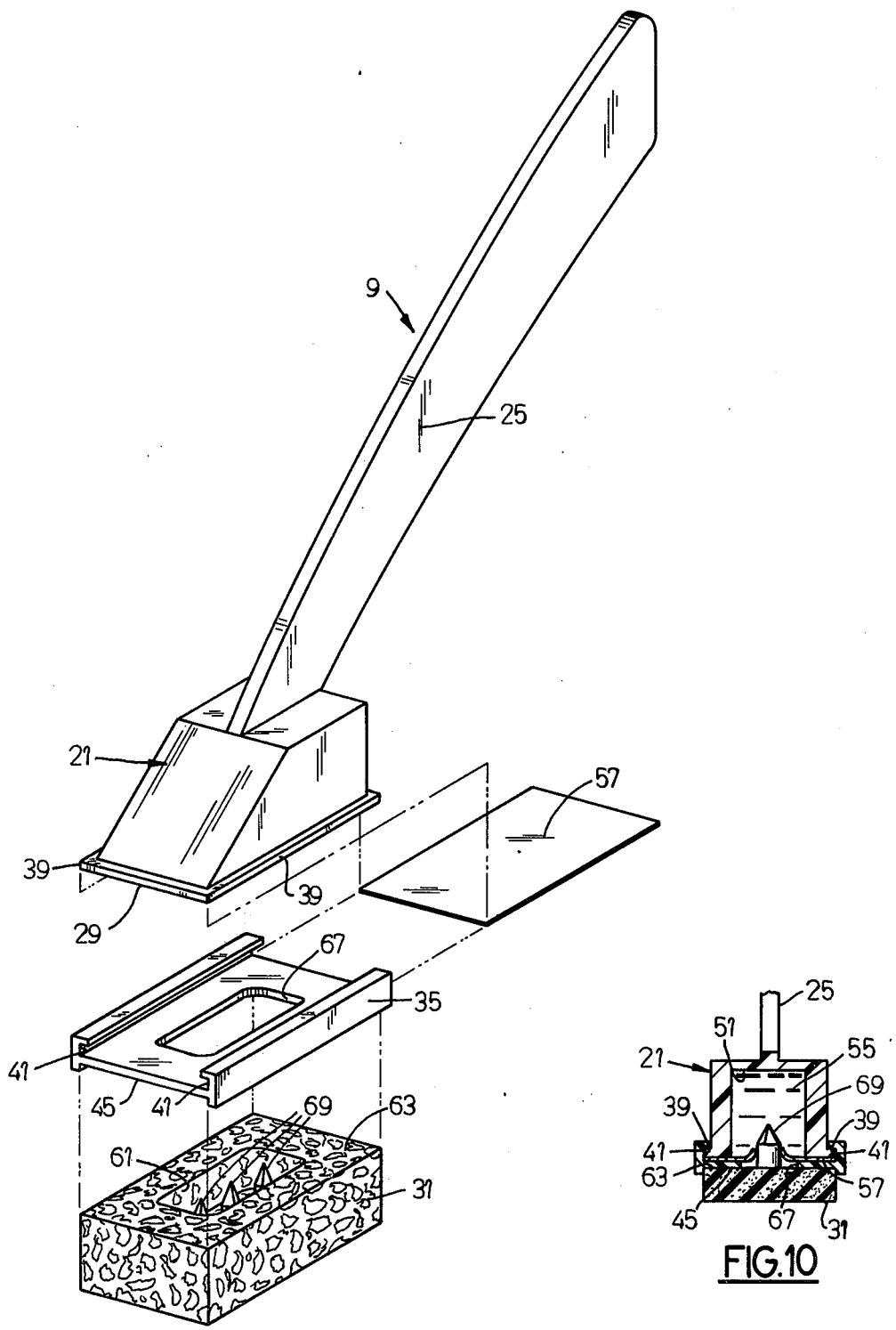
FIG. 10 is a cross-sectional view of the device shown in FIG. 1 taken along the line 10—10 thereof, when the sponge has been compressed.
FIG. 11 is an exploded perspective view showing the relationship of the several elements of the device of FIG. 1.

Bottom surface 29 has lateral extensions 39, best seen in FIGS. 2 and 11, which are complementary to grooves 41 of sponge holder 35. By sliding lateral extensions 39 along grooves 41, sponge 31 and sponge holder 35 are mounted on lateral extensions 39 and affixed to bottom surface 29 of base receptacle 21.

Preferably base receptacle 21 and handle 25 are made of a styrenic material; e.g., ABS copolymers made from acrylonitrile, butadiene and styrene; or polystyrene, while sponge 31 is made of open cell polyurethane. Advantageously, sponge 31 can be solvent sealed or adhered to the bottom of sponge holder 35 and sponge holder 35 can be solvent sealed or adhered to lateral extension 39 of base receptacle 21. However, it will be obvious to those skilled in the art that sponge 31, sponge holder 35 and lateral extensions 39 can be mechanically affixed to their respective mates, if so desired.

Base receptacle 21 has a reservoir 51 opening to bottom surface 29 and adapted to hold a predetermined amount of antiseptic solution. Preferably, reservoir 51 can hold from 2–5 ml. of solution. The preferred antiseptic solutions are betadine, benzalkonium chloride, poloxamer iodine and thimerosal.

As best seen in FIG. 10, after the antiseptic solution 55 is poured into reservoir 51, reservoir 51 is covered by a frangible material 57 which is adhered to bottom surface 29 of base receptacle 21. Frangible material 57 can be any plastic or metal material and, preferably, is made of aluminum foil.

Figure 6:
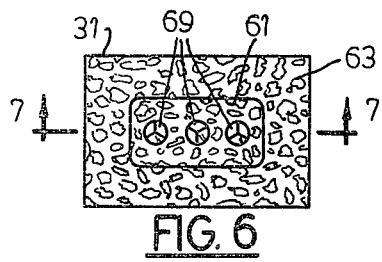
FIG. 6 is a top plan view of the sponge of the device of FIG. 1.
Figure 7:
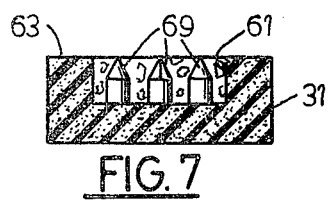
FIG. 7 is a cross-sectional view of the sponge of FIG. 6 taken along line 7—7 thereof.
Figure 8:
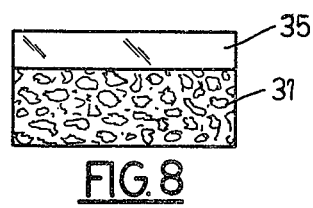
FIG. 8 is a front elevational view of the sponge and sponge holder of the device of FIG. 1.

As best seen in FIGS. 6 and 7, sponge 31 has a cavity 61 recessed from its upper surface. When sponge 31 is affixed to sponge holder 35, bottom surface 45 of sponge holder 35 is juxtaposed with upper surface 63 of sponge 31. Further, aperture 67 of sponge holder 35 is spatially aligned with cavity 61 of sponge 31.

Figure 9:
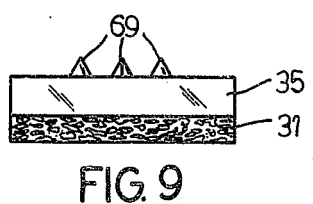
FIG. 9 is a front elevational view of the sponge and sponge holder shown in FIG. 8 when the sponge has been compressed.

Cavity 61 has a plurality of truncated or sharpened rods 69 extending upwardly from its bottom wall to provide means for piercing frangible cover 57. Rods 69 can be separate from each other or integral to a common base. Rods 69 are affixed to the bottom wall of cavity 61, preferably by solvent sealing, and when sponge 31 is compressed, as shown in FIGS. 9 and 10, rods 69 extend out of cavity 61 entirely through sponge holder aperture 67 and through frangible cover 57. It will be readily apparent that when rods 69 pierce frangible cover 57, antiseptic solution 55 is released from reservoir 51 into cavity 61 of sponge 31.

Preferably, rods 69 will be separated a distance sufficent to cause frangible cover 57 to tear a ragged hole in cover 57, so that the antiseptic solution can readily readily flow from reservoir 51 without regard to the surface tension of the solution. Rods 69 can be advantageously made from high impact polystyrene. It will be readily apparent to those skilled in the art that various pins, points, needles or other piercing means can be used in place of rods 69 to pierce frangible cover 57.

Having described the invention in specific detail and exemplified the manner in which it may be carried into practice, it will now be readily apparent to those skilled in the art that innumerable variations, applications, modifications and extensions of the basic principles involved may be made without departing from its sphere or scope.

That which I claim is:

1. In a tool for surgical preparations including a base receptacle having a bottom surface adapted to receive a sponge, a handle upstanding from said base receptacle adapted for hand manipulation of said tool and a sponge affixed to said bottom surface, the improvements which comprises:
   a reservoir in said base receptacle having an opening to said bottom surface and adapted to hold a predetermined amount of antiseptic solution,
   a frangible cover over secured said opening to said bottom surface,
   said predetermined amount of antiseptic solution contained in said reservoir by said cover,
   said sponge affixed to a sponge holder means which has a pair of longitudinal grooves complementary to and slidably mounted on lateral extensions of said bottom surface of said base receptacle,
   a cavity in said sponge recessed from and opening toward said bottom surface of said base receptacle, and
   an upwardly extending piercing means disposed in said cavity and adapted to pierce said frangible cover when said sponge is compressed against said bottom surface of said base receptacle to thereby release said antiseptic solution from said reservoir into said cavity of said sponge.

* * * * *